US006223070B1

(12) United States Patent
Chait

(10) Patent No.: US 6,223,070 B1
(45) Date of Patent: *Apr. 24, 2001

(54) INDWELLING CATHETER

(75) Inventor: Peter G. Chait, Thornhill (CA)

(73) Assignee: Cook, Inc., Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/344,838

(22) Filed: Jun. 28, 1999

Related U.S. Application Data

(63) Continuation of application No. 09/039,639, filed on Mar. 16, 1998, now Pat. No. 5,941,823.

(51) Int. Cl.[7] .................................................. A61F 2/02
(52) U.S. Cl. ............................................. 600/433; 604/32
(58) Field of Search .............................. 600/32, 31, 434, 600/433; 604/180, 246, 247

(56) References Cited

U.S. PATENT DOCUMENTS

| 3,680,562 | 8/1972 | Wittes et al. | 604/51 |
|---|---|---|---|
| 4,381,765 | * 5/1983 | Burton | 600/32 |
| 5,702,371 | * 12/1997 | Bierman | 604/180 |
| 5,713,877 | * 2/1998 | Davis | 604/246 |
| 5,718,686 | * 2/1998 | Davis | 601/101 |
| 5,718,691 | * 2/1998 | Russo | 604/247 |

* cited by examiner

Primary Examiner—Cary O'Connor
Assistant Examiner—Pamela L. Wingood
(74) Attorney, Agent, or Firm—Woodard, Emhardt, Naughton, Moriarty & McNett

(57) ABSTRACT

An indwelling catheter having an extremely low profile proximal section. The indwelling catheter of the present invention solves the problems associated with the prior art feeding catheters by providing an extremely low profile proximal section which is situated external to the patient's body when the catheter is in place. The external portion is preferably in the form of a "trap door", including a flat base portion that lies against the patient's skin and a flat, hinged cover which is operative to seal the proximal opening of the catheter when not in use. In order to retain the catheter and prevent it from being accidentally dislodged, the catheter includes a series of helical coils which are unformed during catheter insertion and then automatically reform in order to hold the catheter in place internally. The catheter is self-adjusting in that fewer or greater loops will automatically reform depending upon the thickness of the patient's abdominal wall. The catheter of the present invention is therefore self-adjusting in order to accommodate the distance between the abdominal wall and the stomach.

21 Claims, 5 Drawing Sheets

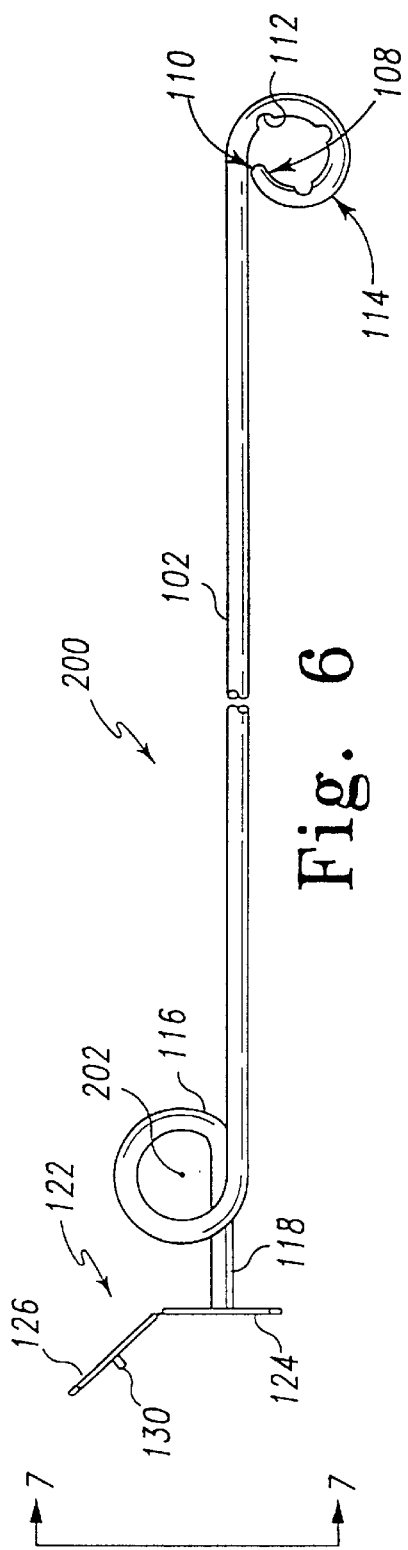
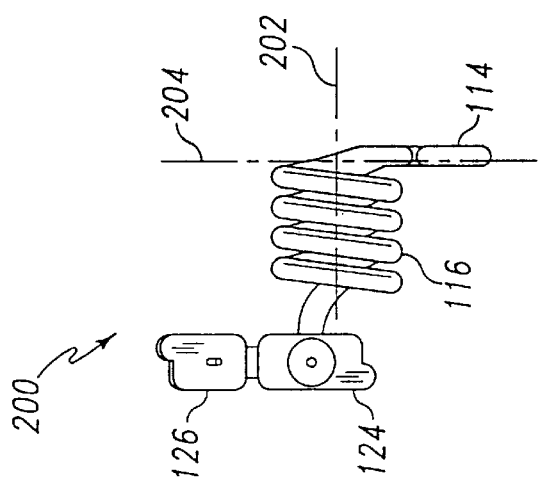

INDWELLING CATHETER

This application is a continuation of Ser. No. 09/039,636 filed Mar. 16, 1998, U.S. Pat. No. 5,941,823.

TECHNICAL FIELD OF THE INVENTION

The present invention generally relates to medical devices and, more specifically, to an indwelling catheter.

BACKGROUND OF THE INVENTION

The following specification, in both the background and in the detailed description, describes the use of the catheter of the present invention in the areas of gastrostomy and gastrojejunostomy and cecostomy. While the present invention finds particular use in these fields, those skilled in the art will recognize that the catheter of the present invention may be used in any application where connection from the outside of the patient's body to an internal cavity within the body is desired, such as in the biliary tree, the liver, the kidney, etc.

With reference to gastrostomy and gastrojejunostomy procedures as a particular example, catheters for use in these procedures are inserted directly through the abdominal wall of the patient and into the stomach. Gastrostomy catheters can then be used for feeding the patient directly into the stomach, wherein nourishing substances are inserted into an external opening in the catheter and are transported by the catheter to the interior of the patient's stomach. With the gastrojejunostomy catheter, the distal portion of the catheter inside the patient is long enough to be positioned in the jejunum, such that feeding can bypass the stomach entirely.

FIG. 1 illustrates a prior art design for such catheters, indicated generally at 10. Because these catheters are left in place for extended periods of time, and because they extend externally from the patient, it is necessary that these catheters have some retention means for preventing the catheter from being accidentally removed from the patient. The catheter 10 of FIG. 1 uses a single, pull string-locked loop inside the stomach for catheter retention. As can be seen by the drawing, the proximal end 12 of the catheter 10, the fitting 14, the pull string 16 and the cuff 18 all protrude out of the patient's abdominal wall for a distance of several centimeters. This protruding proximal catheter section can be a source of great distress for many patients. In addition to the emotional stress of having a catheter tube protruding from the stomach, nearly all patients find that lying on the catheter or covering the catheter is uncomfortable. Such prior art catheters are particularly problematic with pediatric patients, who cannot leave the catheter alone and will usually end up pulling the catheter out.

There is therefore a need for a catheter which is designed to extend from an interior cavity of the patient to a point external of the patient, wherein the portion of the catheter which lies external to the patient is minimized. In addition, the catheter must provide means for securely anchoring the catheter in place, such that it is difficult for the catheter to be accidentally removed. The present invention is directed toward meeting these needs.

SUMMARY OF THE INVENTION

The present invention relates to an indwelling catheter having an extremely low profile proximal section which is situated external to the patient's body when the catheter is in place. The external portion is preferably in the form of a "trap door", including a flat base portion that lies against the patient's skin and a flat, hinged cover which is operative to seal the proximal opening of the catheter when not in use. In order to retain the catheter and prevent it from being accidentally dislodged, the catheter includes a series of helical coils which are unformed during catheter insertion and then automatically reform in order to hold the catheter in place internally. The catheter is self-adjusting in that fewer or greater loops will automatically reform depending upon the thickness of the patient's abdominal wall. The catheter of the present invention is therefore self-adjusting in order to accommodate the distance between the abdominal wall and the stomach.

In one form of the invention an indwelling catheter is disclosed, comprising an elongate body having a proximal end, a distal end and an interior lumen therethrough; an external flange coupled to the proximal end; and a plurality of helical coils formed in the body between the proximal and distal ends; wherein the helical coils may be straightened out by placing a stiffener into the interior lumen in order to facilitate placement of the catheter between an external surface of a patient and an interior cavity thereof; and wherein at least one of the helical coils automatically reforms when the stiffener is removed from the interior lumen after placement of the catheter, such that the flange is held against the external surface of the patient and the at least one helical coil is held against an interior surface of the cavity.

In another form of the invention a method of placing an indwelling catheter is disclosed, comprising the steps of: (a) providing an indwelling catheter, comprising an elongate body having a proximal end, a distal end and an interior lumen therethrough; an external flange coupled to the proximal end; and a plurality of helical coils formed in the body between the proximal and distal ends; (b) inserting a stiffener into the interior lumen such that the helical coils are straightened out; (c) inserting the catheter/stiffener through an external surface of a patient such that the distal end of the elongate body lies within an internal cavity of the patient and the external flange abuts the external surface of the patient; and (d) holding the elongate body in place while withdrawing the stiffener from the interior lumen, such that at least one of the helical coils reforms within the internal cavity, such that the flange is held against the external surface of the patient and the at least one helical coil is held against an interior surface of the cavity.

In another form of the invention an indwelling catheter is disclosed, comprising an elongate body having a proximal end, a distal end and an interior lumen therethrough; and a substantially flat external flange coupled to the proximal end, wherein the flange comprises a substantially flat base; a substantially flat cover; and a hinge coupling the cover to the base.

BRIEF DESCRIPTION OF THE DRAWINGS

FIG. 6 is a side elevational view of a second embodiment catheter of the present invention.

FIG. 7 is an end elevational view of the second embodiment view catheter of the present invention.

DETAILED DESCRIPTION OF THE PREFERRED EMBODIMENT

Figure 1:
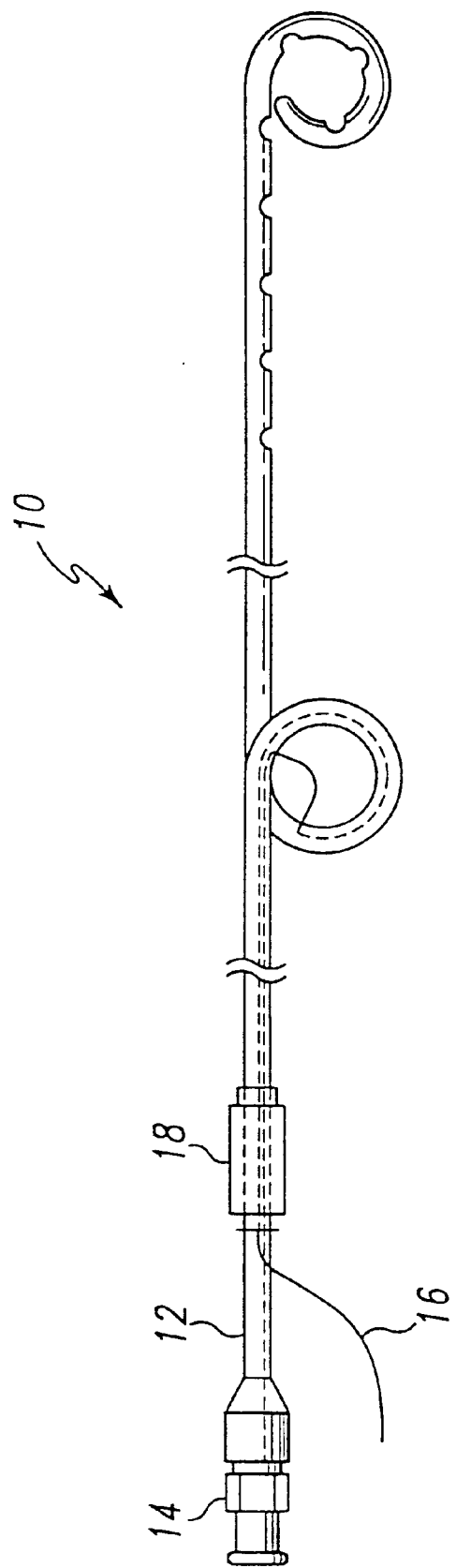
FIG. 1 is a side elevational view of a prior art catheter device.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The indwelling catheter of the present invention solves the problems associated with the prior art feeding catheters by providing an extremely low profile proximal section which is situated external to the patient's body when the catheter is in place. The external portion is preferably in the form of a "trap door", including a flat base portion that lies against the patient's skin and a flat, hinged cover which is operative to seal the proximal opening of the catheter when not in use. In order to retain the catheter and prevent it from being accidentally dislodged, the catheter includes a series of helical loops which are unformed during catheter insertion and then automatically reform in order to hold the catheter in place internally. The catheter is self-adjusting in that fewer or greater loops will automatically reform depending upon the thickness of the patient's abdominal wall. The catheter of the present invention is therefore self-adjusting in order to accommodate the distance between the abdominal wall and the stomach.

Figure 2:
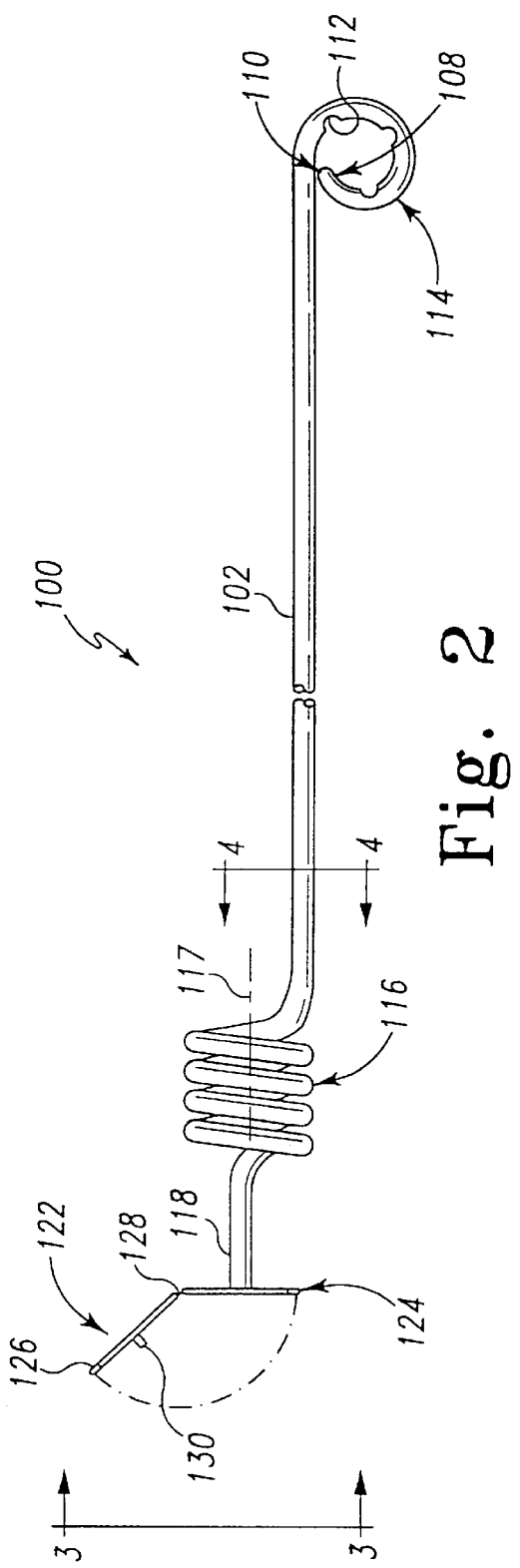
FIG. 2 is a side elevational view of a preferred embodiment catheter of the present invention.

Referring now to FIG. 2, there is illustrated a preferred embodiment of the indwelling catheter of the present invention, indicated generally at 100. The catheter 100 comprises an elongated tube 102 having an open central lumen 104 (see FIG. 4) extending therethrough. The tube 102 may be made from any flexible, biologically compatible material such as polyurethane. The proximal end of the tube 102 includes an opening 106 (see FIG. 3) which communicates with the lumen 104. The distal end 108 of the tube 102 is preferably tapered and includes an axially directed end hole 110. The tube 102 further includes a plurality of side ports 112 within the distal pigtail 114. The end hole 110 and the side ports 112 provide paths for fluid communication between the interior lumen 104 and the outside of the catheter 100.

Figure 5:
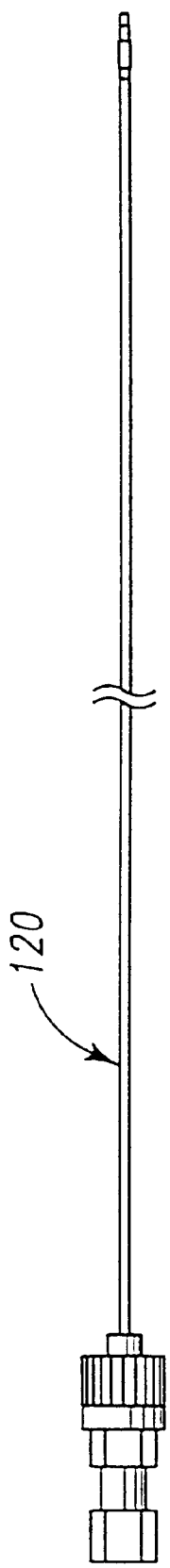
FIG. 5 is a side elevational view of a metal stiffener used for inserting the catheter of the present invention into the patient over a wire guide.
Figure 8:
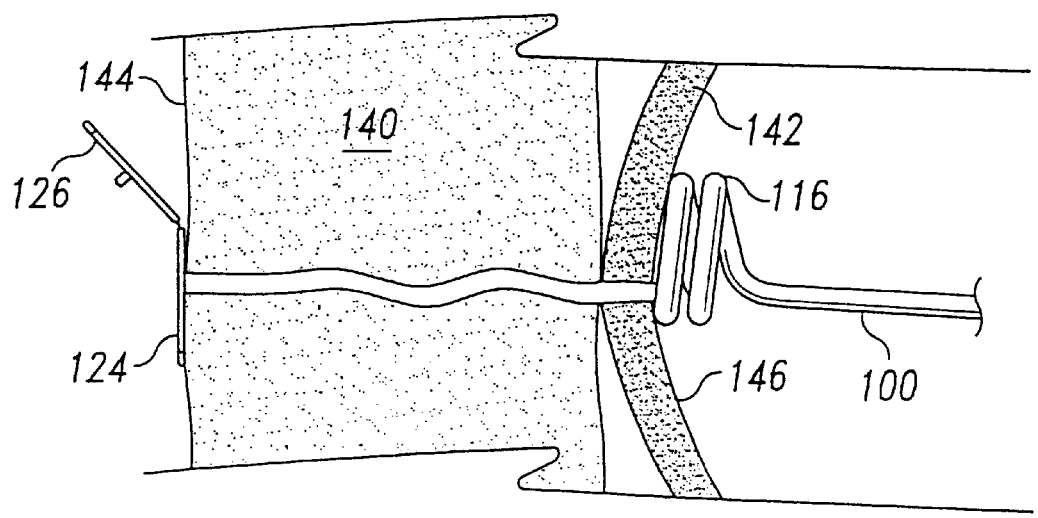
FIG. 8 is a partial cross-sectional view of the preferred embodiment catheter of the present invention inserted into a patient's stomach.
Figure 9:
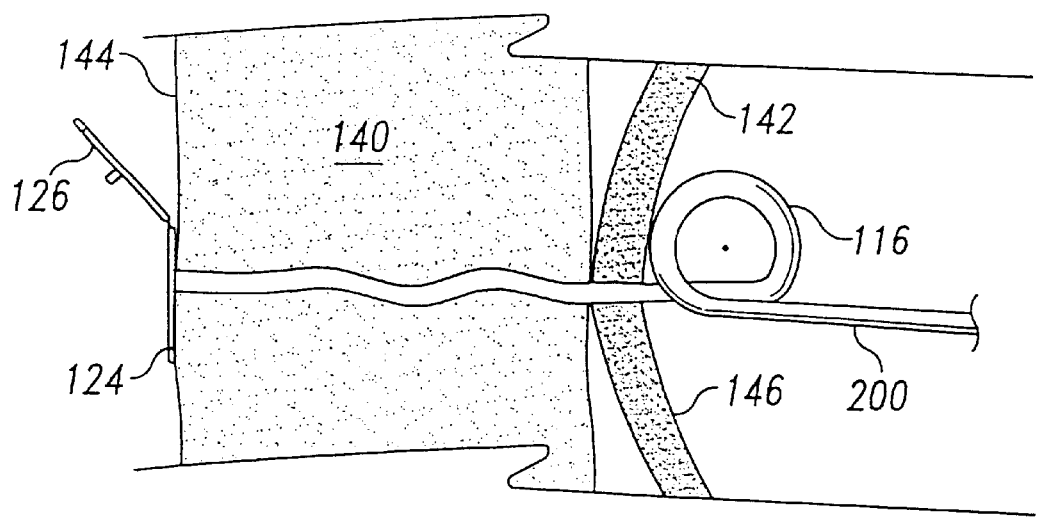
FIG. 9 is a partial cross-sectional view of the second embodiment catheter of the present invention inserted into a patient's stomach.

The catheter 100 includes a distal pigtail loop 114 so that the internal end of the catheter will be blunt and non-irritating. The catheter 100 further includes several helically wound loops 116 near the proximal end of the catheter 100. In the preferred embodiment, the catheter has four such loops 116. A short, substantially straight section 118 of the catheter 100 lies between the helical loops 116 and the proximal end of the catheter. Both the distal pigtail 114 and the helical loops 116 are formed in the catheter 100 such that they will straighten out when a metal stiffener 120 (see FIG. 5) is inserted into the central lumen 104 of the catheter, and will then automatically reform when the metal stiffener 120 is removed from the catheter 100.

Figure 3:
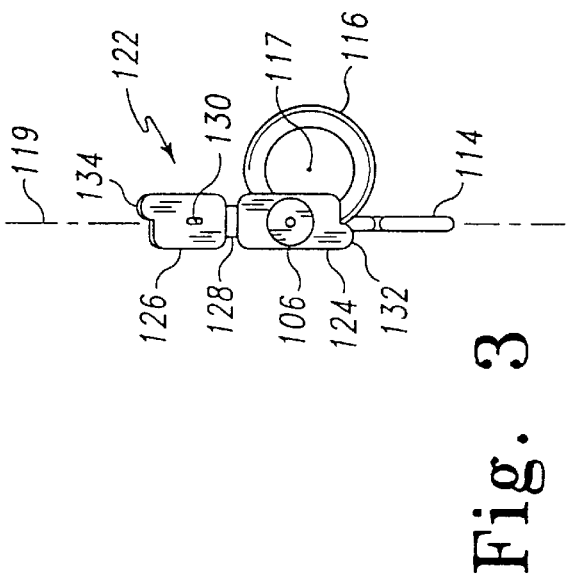
FIG. 3 is an end elevational view of the preferred embodiment catheter of the present invention.
Figure 4:
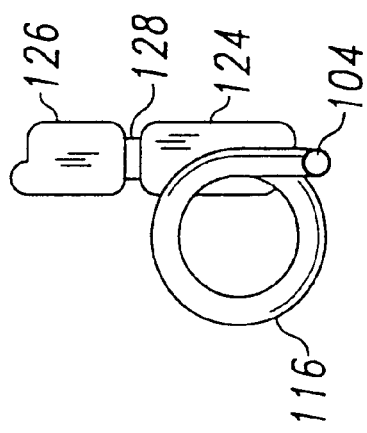
FIG. 4 is a cross-sectional view of the preferred embodiment catheter of the present invention.

Referring to FIG. 3, it can be seen that the helical coils 116 have a central axis 117 about which they are positioned. The remainder of the catheter body 102, from the proximal section 118 to the distal pigtail 114, lies substantially within a plane 119. In the preferred embodiment of the present invention, the central axis 117 of the helical coils 116 is either substantially parallel to the plane 119 or lies substantially within the plane 119, but is not perpendicular to the plane 119.

A second embodiment of the indwelling catheter of the present invention is illustrated in FIGS. 6 and 7, and indicated generally at 200. The catheter 200 is identical to the catheter 100, with the exception that the central axis 202 of the helical coils 116 is formed substantially perpendicular to the plane 204 in which most of the catheter body lies. Operation and placement of the catheter 200 is analogous to the operation and placement of the catheter 100.

The proximal end of the catheter 100 preferably includes a flange 122 that sits substantially flush with the exterior surface of the patient's skin when the catheter 100 is in place. The flange 122 is designed so as to minimize the amount of the catheter 100 which protrudes away from the patient's abdominal wall. In a preferred embodiment, the flange 122 comprises a substantially flat base portion 124 which is integrally formed as a single unit with the catheter 100. The opening 106 into the central lumen 104 passes through the base portion 124. The base portion 124 is preferably rectangular in shape, having dimensions of 1.5 cm.×2.5 cm.×2 mm. The flange 122 further preferably includes a similarly sized cover 126 which is coupled to the base portion 124 by an integrally formed hinge 128. The cover 126 includes a protrusion 130 thereon which is placed so as to plug the opening 106 when the cover 126 is mated with the base portion 124. The diameter of the opening 106 and the diameter of the protrusion 130 are chosen such that they couple in an interference fit, thereby prohibiting fluid leakage from the catheter 100 when the cover 126 is in place. The base 124 further includes a tab 132 and the cover 126 includes a complimentary tab 134 in order to facilitate separation of the cover 126 from the base 124.

A preferred use for the indwelling catheter 100 of the present invention is for access to the gastrointestinal tract from outside of a patient, although those skilled in the art will recognize the use of the present invention for access to other body cavities is analogous. When used as a gastrojejunostomy catheter, the catheter 100 preferably has an overall length of 32 cm. with all of the coils 116 reformed and the distal pigtail 114 reformed. The distance from the base 124 of the flange 122 to the first of the helical loops 116 is preferably in the range of 0.5–3 cm. The distance from the most distal of the helical coils 116 to the distal end of the catheter 100 is preferably 27 cm., but can be sized differently according to the size of the patient. In this configuration, the catheter 100 is long enough such that its distal end can be positioned in the jejunum and feeding through the catheter can bypass the stomach. In order to use the catheter 100 as a gastrostomy catheter, it is only necessary that the distance between the helical coils 116 and the distal end be removed, allowing the catheter 100 to be used for feeding directly into the stomach. The catheter 100 is further particularly adapted for use as a cecostomy catheter for providing access to the cecum. The catheter for such gastrointestinal applications is preferably 10 fr. in size, but other sizes may be used depending upon patient size.

In order to position the catheter 100 within the patient, the metal stiffening tube 120 is inserted into the proximal opening 106 and pushed all the way to the distal tip 108 of the catheter 100. This will cause the coils 116 and the distal pigtail 114 to completely straighten out. The catheter 100, with the metal stiffener 120 in place, may then be inserted over a wire guide through the patient's abdominal wall and positioned under fluoroscopic control until the distal end is at the desired location within the patient. At this point, the base 124 of the flange 122 will be flush against the exterior surface of the patient's abdominal wall. The metal stiffener 120 and the wire guide are then removed from the catheter, allowing the distal pigtail 114 to reform and further allowing one or more of the helical coils 116 to reform.

The catheter 100 is illustrated in FIG. 6 as being placed through the abdominal wall 140 and stomach 142 of a patient. The illustration shows the catheter 100 after the metal stiffening tube 120 has been removed therefrom. It can be seen from this illustration that upon removal of the metal stiffening tube 120, only two of the four original helical coils 116 have reformed in the catheter. This is because the thickness of the abdominal wall 140 is such that the remaining two helical coils 116 must remain unwound in order for the catheter 100 to traverse the distance between the exterior surface 144 of the abdominal wall 140 to the interior surface 146 of the stomach 142. Therefore, by placing a plurality of helical loops 116 in the catheter 100, the catheter is made substantially universal in terms of patient size. Depending upon the thickness of the abdominal wall 140, a greater or lesser number of the loops 116 will reform within the stomach. For a small patient, all of the helical loops 116 will reform in the stomach, while for a larger patient, only a few of the loops 116 will reform. The result is that the catheter 100 adjusts itself to accommodate the distance between the exterior abdominal wall 144 and the interior of the stomach 146. The reforming of the helical loops 116 within the stomach 142 act to retain tension between the base 124 in order to hold it securely in place at the surface 144. It will be appreciated by those skilled in the art that although the catheter 100 was illustrated in the preferred embodiment as having four helical loops 116, the present invention comprehends the catheter having a greater or lesser number of helical loops 116.

It will be appreciated with reference to FIG. 6 that once the catheter 100 has been positioned, the only portion of the catheter 100 which remains external to the patient is set flush with the patient's skin so that there is nothing protruding away from the patient's abdominal wall. This is psychologically beneficial for the patient, plus it minimizes the chance of pediatric patients being able to grasp the proximal end of the catheter and pull it out. As an additional precaution, the entire proximal end of the catheter can be covered and kept out of sight by placing a small bandage thereover when not in use. As a further precaution, a piece of hypoallergenic two-sided tape (such as DUODERM) may be placed between the base portion 124 and the patient's skin.

FIG. 7 illustrates the second embodiment catheter 200 inserted into a patient's stomach in a manner analagous that of FIG. 6. It can be seen that at least one of the helical coils 116 have reformed, thereby securing the catheter 200 in place.

When the catheter 100 is not in use, the cover 126 is kept in place on the base 124, sealing the proximal opening 106. When it is desired to introduce fluids into the body through the catheter 100, the cover 126 is lifted, thereby exposing the proximal opening 106. The catheter may then be accessed with, for example, a 14 gauge blunt tipped needle or a 14 gauge plastic cannula.

An additional feature of the present invention is that patient's frequently have several long term indwelling catheters in place for different purposes. Some may be for infusion of chemotherapeutic drugs and others may be for feeding. In such situations, there is a very real danger of confusing which catheter is for which purpose, making it possible to inject feed into the venous system or chemotherapy drugs into the stomach, both of which can be a potentially fatal mistake. If the catheter 100 of the present invention is used for feeding, its exterior flange 122 is unlike any other indwelling catheter that the patient is likely to have inserted, therefore the likelihood of a parent or night shift nurse-aide connecting to the wrong catheter is greatly reduced or even eliminated. Furthermore, if more than one of the catheters of the present invention are being used in the same patient for different purposes, the cover 126 provides a convenient surface for labelling the catheter in order to minimize confusion as to its purpose.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. For example, the preferred embodiment catheter has been described for use in the gastrointestinal tract, however it may be used in any procedure where it is desired to maintain continuing access from the exterior of a patient to an internal body cavity.

What is claimed is:

1. An indwelling catheter, comprising:

an elongate body having a proximal end, a distal end and an interior lumen therethrough; and at least one helical coil formed in the body between the proximal and distal ends;

wherein the at least one helical coil may be straightened out by placing a stiffener into the interior lumen in order to facilitate placement of the catheter between an external surface of a patient and an interior cavity thereof; and wherein the at least one helical coil automatically reforms when the stiffener is removed from the interior lumen after placement of the catheter, such that the at least one helical coil is held against an interior surface of the cavity.

2. The indwelling catheter of claim 1, wherein a central axis of the at least one helical coil is substantially parallel to a plane in which a remainder of the elongate body lies.

3. The indwelling catheter of claim 1, wherein a central axis of the at least one helical coil is substantially perpendicular to a plane in which a remainder of the elongate body lies.

4. The indwelling catheter of claim 1, further comprising:

an external flange coupled to the proximal end;

wherein the at least one helical coil automatically reforms when the stiffener is removed from the interior lumen after placement of the catheter, such that the flange is held against the external surface of the patient; and wherein the external flanges lies substantially flush with the external surface of the patient.

5. The indwelling catheter of claim 4, wherein the external flange further comprises:

a substantially flat base;

a substantially flat cover; and a hinge coupling the cover to the base whereby the cover operates to prevent fluid leakage externally of the catheter.

6. The indwelling catheter of claim 5, further comprising:

a hole through the base and in fluid communication with the interior lumen; and a protrusion on the cover operative to close the hole when the cover is placed over the base.

7. The indwelling catheter of claim 4, wherein the external flange is integrally formed with the elongate body.

8. The indwelling catheter of claim 1, further comprising a plurality of sideports formed in the body and providing a fluid flow path between the interior lumen and an exterior of the catheter.

9. The indwelling catheter of claim 1, wherein the at least one helical coil is spaced from the proximal end by a substantially straight section of the body.

10. A method of placing an indwelling catheter, comprising the steps of:

(a) providing an indwelling catheter, comprising:
   an elongate body having a proximal end, a distal end and an interior lumen therethrough; and
   at least one helical coil formed in the body between the proximal and distal ends;

(b) inserting a stiffener into the interior lumen such that the at least one helical coil is straightened out;

(c) inserting the catheter/stiffener through an external surface of a patient such that the distal end of the elongate body lies within an internal cavity of the patient; and (d) holding the elongate body in place while withdrawing the stiffener from the interior lumen, such that the at least one helical coil reforms within the internal cavity, such that the at least one helical coil is held against an interior surface of the cavity.

11. The method of claim 10, wherein step (c) is performed over a wire guide.

12. The method of claim 10, wherein step (c) is performed under fluoroscopic control.

13. An indwelling catheter, comprising:

an elongate body having a proximal end, a distal end and an interior lumen therethrough; and an external flange coupled to the proximal end such that the elongate body does not extend proximal to the flange, wherein the flange comprises:
a base; and
a cover releasably engaging the base;

whereby the cover operates to prevent fluid leakage externally of the catheter.

14. The indwelling catheter of claim 13, further comprising:

at least one helical coil formed in the body between the proximal and distal ends;

wherein the at least one helical coil may be straightened out by placing a stiffener into the interior lumen in order to facilitate placement of the catheter between an external surface of a patient and an interior cavity thereof; and wherein the at least one helical coil automatically reforms when the stiffener is removed from the interior lumen after placement of the catheter, such that the flange is held against the external surface of the patient and the at least one helical coil is held against an interior surface of the cavity.

15. The indwelling catheter of claim 14, wherein a central axis of the at least one helical coil is substantially parallel to a plane in which a remainder of the elongate body lies.

16. The indwelling catheter of claim 14, wherein a central axis of the at least one helical coil is substantially perpendicular to a plane in which a remainder of the elongate body lies.

17. The indwelling catheter of claim 13, wherein the external flange lies substantially flush with the external surface of the patient.

18. The indwelling catheter of claim 13, further comprising:

a hole through the base and in fluid communication with the interior lumen; and a protrusion on the cover operative to close the hole when the cover is placed over the base.

19. The indwelling catheter of claim 13, wherein the external flange is integrally formed with the elongate body.

20. The indwelling catheter of claim 13, further comprising a plurality of sideports formed in the body and providing a fluid flow path between the interior lumen and an exterior of the catheter.

21. The indwelling catheter of claim 14, wherein the at least one helical coil is spaced from the proximal end by a substantially straight section of the body.

\* \* \* \* \*